United States Patent [19]

Tesarik et al.

[11] 4,014,793
[45] Mar. 29, 1977

[54] DETECTING APPARATUS FOR LIQUID CHROMATOGRAPHY

[75] Inventors: Karel Tesarik; Milos Krejci, both of Brno, Czechoslovakia

[73] Assignee: Ceskoslovenska akademie ved, Praha, Czechoslovakia

[22] Filed: May 21, 1975

[21] Appl. No.: 579,683

[30] Foreign Application Priority Data

May 21, 1974 Czechoslovakia ............... 3601/74

[52] U.S. Cl. .......................... 210/198 C; 23/253 R
[51] Int. Cl.$^2$ ........................................ B01D 15/08
[58] Field of Search .......... 210/31 C, 24 C, 198 C; 55/67, 197, 386; 23/232 C, 253 A; 73/23.1, 61.1 C

[56] References Cited
UNITED STATES PATENTS 3,463,615  8/1969  Solhor ..................... 210/198 C
3,578,785  5/1971  Patterson .................. 210/198 C Primary Examiner—John Adee

[57] ABSTRACT

An improved detection apparatus employable in liquid chromatography for analyzing a selected non-volatile phase of a liquid effluent is described. A vibrating capillary tube is coupled to the effluent source for atomizing the effluent. The atomizer communicates with a first end of a heated separation column, which is in further communication with a carrier gas source. The non-selected components of the effluent are volatilized in the separation column, while the non-volatilized phase is propelled by means of the carrier gas out of the separation column and through a suitable sensor via a control valve such as a diaphragm. The sensed selected phase is thereupon recorded and analyzed in a conventional manner.

5 Claims, 2 Drawing Figures

DETECTING APPARATUS FOR LIQUID CHROMATOGRAPHY

BACKGROUND OF THE INVENTION

The invention relates to a detecting arrangement used in liquid chromatography for the analysis of a selected non-volatile phase of a liquid effluent.

Detecting arrangements in most common use in the field of liquid chromatography are the so-called transport detectors. The main part of a transport detector is a mechanical conveyor (embodied, e.g. by a wire, band, chain or rotating grid) to which the effluent is applied. Such effluent is transmitted by the conveyor from a source of the effluent (e.g. a column of the liquid chromatograph) to a separator, where the volatile phase is separated from the desired component to be analyzed. The conveyor thereupon carries the desired component to a gasifier, and the resulting gasified component is introduced to a sensing device (e.g. a pair of electrodes). The response of the sensing device to the passage of the selected components is thereupon registered by a recorder connected electrically with the electrodes for further analysis.

One disadvantage of such arrangements when used in liquid chromatography is that they have a sensitivity which is at best 2-4 orders lower than that obtainable in gas chromatography meassurements using the same sensors. Moreover, such arrangements cannot effect a high degree of gasification of the selected phase, so that the usable sample of the selected component introduced to the sensor is small; this is particularly true if the conveyor is not completely wetted by the effluent.

Additionally, problems have been found to occur with the conveyor of the transport regarding its cleaning, its preparation for the repeated transmission of samples to be analyzed, and in the selection of its materials for the good mechanical and heat resistant properties necessary to accommodate its repeated passage through the hot gasification zone. Also, in this connection facilities must be provided to assure a constant rate of advance of the conveyor.

SUMMARY OF THE INVENTION

Such disadvantages attendant upon the use of mechanical conveyors are overcome with the use of the liquid chromatography detection apparatus in accordance with the instant invention. The effluent is initially atomized by means of a vibratory capillary tube, and the atomized effluent is introduced into one end of a separating column. The separating column is heated to volatilize the non-selected components of the effluent, such volatilized component being cooled and stored in facilities coupled to the separation chamber.

A source of carrier gas is also coupled to the separation chamber for propelling the non-volatilized desired component of the effluent out of the separation chamber and toward the sensor by means of a diaphragm or similar regulation valve. The carrier gas source may be coupled either to the same end of the separating chamber as that to which the capillary tube of the atomizer is coupled, or to the opposite end of such chamber.

The atomizing and pneumatic transmission scheme of the invention results in a much faster and simpler transmission and separation of the desired phase than that possible with the mechanical conveyors of the prior art. Additionally, its sensitivity is at least one order of magnitude higher than that of the prior art, and operates either with the entire effluent or with any desired fraction thereof. Moreover, it optimizes the recovery and cooling of the volatilized component of the effluent.

BRIEF DESCRIPTION OF THE DRAWING

The invention is further set forth in the following detailed description taken in conjunction with the appended drawing, in which.

DETAILED DESCRIPTION

Figure 1:
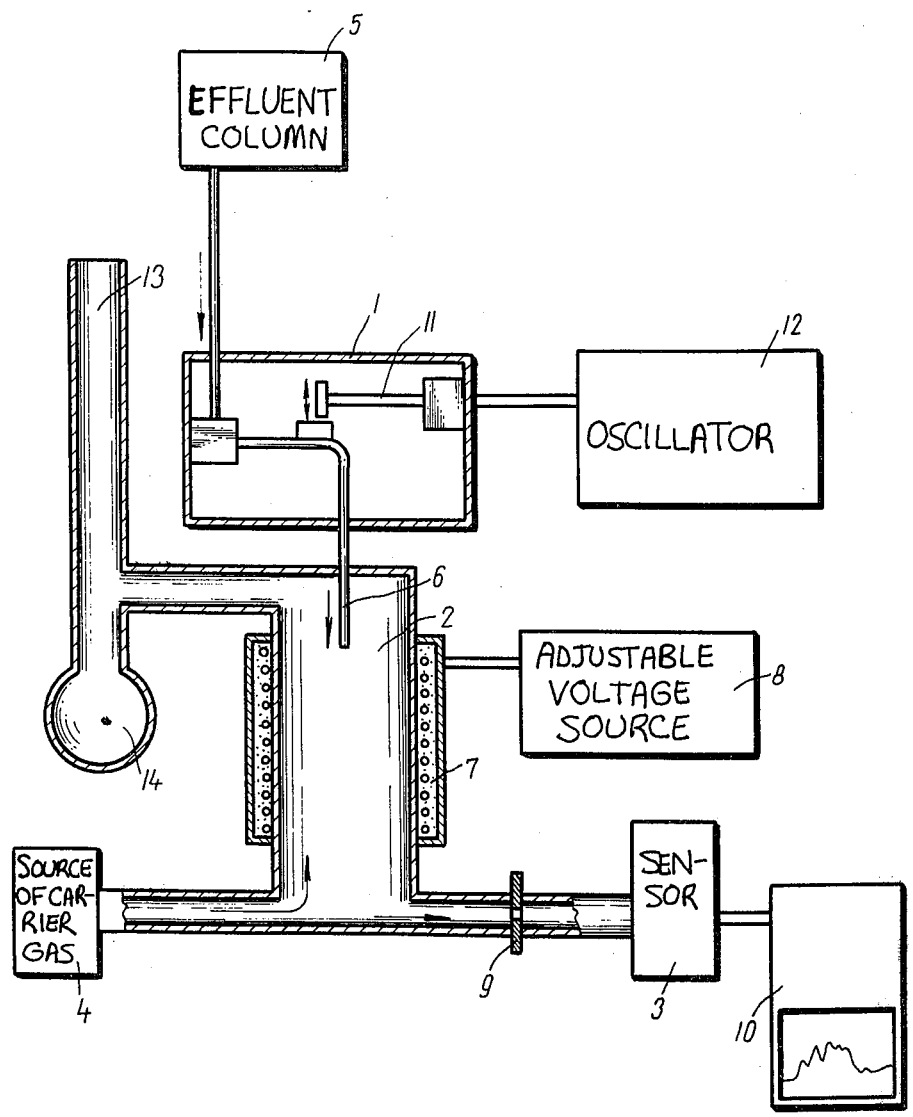
FIG. 1 is a representation, partly in schematic form, of a first embodiment of liquid chromatography detection apparatus in accordance with the invention.

Referring first to the embodiment of the invention shown in FIG. 1, a source of effluent which contains a desired non-volatile component to be analyzed via liquid chromatography techniques is contained in a column 5 of the liquid chromatograph. The column 5 is connected to an atomizer 1 consisting substantially of a capillary 6 controlled by a vibrating device 11, which in turn is connected electrically with an oscillator 12. The capillary 6 has a nozzle communicating with the top of a separating column 2, which is surrounded by an oven 7 controlled by an adjustable voltage source 8. The bottom of the separating column 2 communicates with a source 4 of a carrier gas (e.g. helium, argon or nitrogen). The outlet of the separating column 2 extends, by way of a diaphragm 9, to a conventional sensor 3 which is electrically coupled to a recording device 10. The top of the separating column 2 is also coupled to a reflux cooler 13 having a storage vessel 14.

The effluent from the column 5 of the liquid chromatograph is dispersed by the atomizer 1 into a large number of droplets of small diameter (e.g. 0.1 – 300 $\mu$m and preferably 5 – 100 $\mu$m), which upon discharge into the separating column 2 form a cloud or aerosol. Depending on the difference of volatility between the component of the effluent to be analyzed (and which may be solid at the temperature inside the heated separating column) and the volatile component to be separated, the volatile component is evaporated more or less completely, so that the cloud is rich in the desired component. Such cloud, separated from the volatile component in the column 2, is propelled out of such column by the carrier gas from the source 4 into the sensor 3. The response of the sensor due to passage of the to-be-analyzed component therethrough is registered in a conventional manner in the recording device 10. The sensor 3 may take a form of a conventional detector, e.g. an ionization detector employed in chromatography or spectral analysis, such as mass spectrometry, flame photometry, atom absorption and the like.

The arrangement of FIG. 1 operates as follows: The effluent flows from the column 5 of the liquid chromatograph into the atomizer 1. The atomizer 1 disperses the continuous stream of liquid leaving the nozzle of the capillary 6. The drops of the effluent leaving the nozzle of the capillary 6 enter the separating column 2. The carrier gas introduced from the source 4 flows upwardly as shown against the capillary 6, so that the gas stream washes the drops exiting from the capillary. The separating column 2 is heated by the oven 7 to a temperature, settable via voltage source 8, suitable for optimizing the volatility of the component to be separated.

The drops of the effluent, now consisting principally of the desired non-volatile component to be analyzed, fall to the bottom of the separating column 2, where they are carried along by the stream of carrier gas to the sensor 3. The propulsion speed is controlled by the diaphragm 9.

The frequency and wavelength of the vibration effected by the device 11 under the control of the oscillator 12 is pre-adjusted in dependence on the speed of the flow and the chemical composition of the volatile phase to optimize the size of the drops on the nozzle of the capillary 6. The vibration frequency W of oscillation is in particular determined by the equation $$W^2 = \frac{T\, i\, k\, J'_m(i k a)}{a^2\, P_2\, J_m(i k a)} (m^2 + k^2 a^2 - 1)$$

where
T is the surface tension,
$P_2$ is the density of the liquid,
a is the radius of the undisturbed liquid stream,
$J_m$ is the m - th order of Bessel's function,
m is the azimuth wave number, and
k is the longitudinal wave number.

The wavelength L corresponding to the maximum value of $a^2$ is $$L = 9.2\, a$$

This is in general the most suitable wavelength for dispersion of the liquid stream.

The separated volatile component in the column 2 is guided to the reflux cooler 13, and the resulting condensate is collected in the storage vessel 14.

The rate I of evaporation of the volatile phase of the effluent from the drops in the separating column 2 is determined by the equation $$I = \frac{4\pi r_d D (pd - P_{oo}) M}{RT}(1 + 0.3\, R_e^{1/2} S_c^{1/2})$$

where
$r_d$ is the radius of the drop,
D is the diffusion coefficient,
$P_d$ is the vapor pressure on the surface of the drop,
$P_{oo}$ is the vapor pressure at the wall of the separating column,
M is the molecular weight,
R is the gas constant,
T is the mean gas temperature,
$R_e$ is Reynold's number, and
$S_c$ is Schmidt's number.

Figure 2:
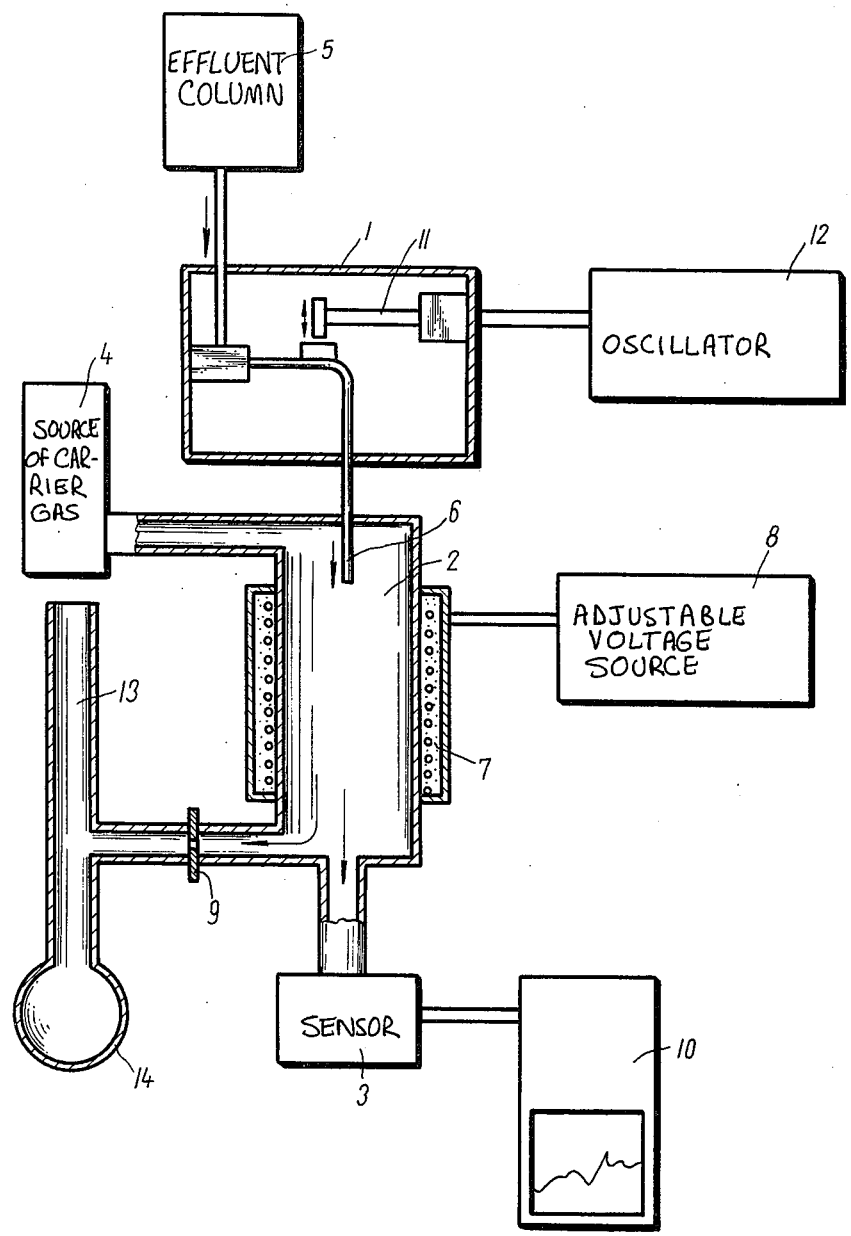
FIG. 2 is a representation, similar to FIG. 1, of an alternate embodiment of a detection apparatus in accordance with the invention.

The arrangement of FIG. 2 is similar to that of FIG. 1, and differs therefrom only in that the reflux tube 13 and storage vessel 14 are coupled via diaphragm 9 to the bottom of separating column 11, while the carrier gas source 4 is coupled to the top thereof. In the case of FIG. 2, the carrier gas flows through the column 2 in the same direction as the droplet stream from the atomizer 1. In all other respects, the function and operation of FIGS. 1 and 2 are analogous.

In the foregoing, several illustrative embodiments of the invention have been described. Many variations and modifications will now occur to those skilled in the art. It is accordingly desired that the scope of the appended claims not be limited to the specific disclosure herein contained.

What is claimed is:

1. In a liquid chromatography detection apparatus for analyzing a selected non-volatile phase of a liquid effluent, comprising a sensor for the selected phase to be analyzed, conveying means for separating the selected phase from the effluent and for passing the separated selected phase to the sensor and means for introducing effluent into the conveying means, the improvement wherein the conveying means comprises, in combination, means coupled to the effluent source for atomizing the effluent, means including a separating column having a first end communicating with the atomizing means for volatilizing the non-selected components of the atomized effluent, a control valve, and means including a carrier gas source isolated from the introducing means and communicating with the separating column for propelling the non-volatilized selected phase from the separating column to the sensor through the control valve.

2. In a liquid chromatography detection apparatus for analyzing a selected non-volatile phase of a liquid effluent, comprising a sensor for the selected phase to be analyzed, and conveying means for separating the selected phase from the effluent and for passing the separated selected phase to the sensor, the improvement wherein the conveying means comprises, in combination, means coupled to the effluent source for atomizing the effluent, means including a separating column having a first end communicating with the atomizing means for volatilizing the non-selected components of the atomized effluent, means including a carrier gas source communicating with the separating column for propelling the non-volatilized selected phase, and means including a control valve for coupling the propelled selected phase from the separating column to the sensor; and in which the apparatus further comprises means coupled to one end of the separating column for cooling and storing the volatilized nonselected components of the effluent.

3. Apparatus as defined in claim 2, in which the propelling means are coupled to the first end of the separating column, and the cooling and storing means are coupled to the end of the separating column opposite to the first end.

4. Apparatus as defined in claim 2, in which the cooling and storing means is coupled to the first end of the separating column, and in which the propelling means are coupled to the end of the separating column opposite to the first end.

5. In a liquid chromatography detection apparatus for analyzing a selected non-volatile phase of a liquid effluent, comprising a sensor for the selected phase to be analyzed, and conveying means for separating the selected phase from the effluent and for passing the separated selected phase to the sensor, the improvement wherein the conveying means comprises, in combination, a capillary tube having a first end coupled to the effluent source for atomizing the effluent, means for vibrating the capillary tube, means including a separating column having a first end communicating with the other end of the capillary tube for volatilizing the non-selected components of the atomized effluent, means including a carrier gas source communicating with the separating column for propelling the non-volatilized selected phase, and means including a control valve for coupling the propelled selected phase from the separating column to the sensor.

* * * * *